United States Patent [19]
Zoeller et al.

[11] Patent Number: 5,821,384
[45] Date of Patent: Oct. 13, 1998

[54] PROCESS FOR GENERATING VINYL CARBOXYLATE ESTERS

[75] Inventors: Joseph Robert Zoeller; Donald Wayne Lane; Eleanor Hawkins Cwirko, all of Kingsport; Dewey Wayne Fuller, Jr., Bristol; Scott Donald Barnicki, Kingsport, all of Tenn.

[73] Assignee: Eastman Chemical Company, Kingsport, Tenn.

[21] Appl. No.: 826,451

[22] Filed: Mar. 27, 1997

[51] Int. Cl.$^6$ ............................ C07C 69/02; C07C 67/12
[52] U.S. Cl. ........................... 560/231; 560/238; 560/261
[58] Field of Search ................................. 560/231, 238, 560/261

[56] References Cited

U.S. PATENT DOCUMENTS

| | | | |
|---|---|---|---|
| 2,425,389 | 8/1947 | Oxley et al. | 260/491 |
| 2,859,241 | 11/1958 | Celanese | 260/491 |
| 5,405,992 | 4/1995 | Funk et al. | 560/265 |

FOREIGN PATENT DOCUMENTS 2013184   12/1977   United Kingdom .

OTHER PUBLICATIONS

Celanese Corporation of America, Vinyl Acetate, Hydrocarbon Processing, vol. 44(11), p. 287, Nov. 1965.

W. Daniels, Kirk–Othmer Encyclopedia of Chemical Technology, 3rd Ed., vol. 23, pp. 817–847 (1978).

C. E. Sumner and Joseph R. Zoeller, Vinyl Acetate in Acetic Acid and Its Derivatives, V. H. Agreda and J. R. Zoeller, eds., Marcel Dekker, NY, Chapter 12, pp. 225–240 (1993).

Hydrocarbon Processing and Petroleum Refiner, vol. 44 (11), p. 287 (1965).

Kirk–Othmer Encyclopedia of Chemical Technology, 3rd Ed., vol. 23 (1978), p. 824.

J. Gauthier–Lafaye and R. Perron, Methanol and Carbonylation, English Translation, Imprimerie CD Editions, Saint–Herblain, France, pp. 201–224 (1987).

*Primary Examiner*—Paul J. Killos
*Assistant Examiner*—Rosalynd Keys
*Attorney, Agent, or Firm*—Michael J. Blake; Harry J. Gwinnell

[57] ABSTRACT

Disclosed is a process for making vinyl carboxylate esters such as vinyl acetate and vinyl propionate, by a reactive distillation process comprising a reaction zone wherein a vinyl carboxylate ester is formed from a carbonyl compound selected from aliphatic aldehydes and ketones and an anhydride of an aliphatic carboxylic acid and a distillation zone from which the vinyl carboxylate ester is recovered and substantially separated from other compounds contained within the column. The process requires significantly less equipment than known, analogous processes and thus the cost of constructing a plant for the operation of the present process is substantially reduced.

19 Claims, 3 Drawing Sheets

PROCESS FOR GENERATING VINYL CARBOXYLATE ESTERS

This invention pertains to a novel process for generating vinyl esters of aliphatic carboxylic acids. More specifically, this invention pertains to producing vinyl carboxylate esters, such as vinyl acetate and vinyl propionate, by a reactive distillation process comprising a reaction zone wherein a vinyl carboxylate ester is formed from an aliphatic carbonyl compound, such as an aldehyde or a ketone, and an anhydride of an aliphatic carboxylic acid, and a distillation zone from which the vinyl carboxylate ester is recovered by substantially separating it from other compounds contained within the column.

BACKGROUND OF THE INVENTION

Vinyl esters, particularly vinyl acetate, are among the most useful industrial organic compounds. Polymers and copolymers of vinyl carboxylate esters are used in coatings, adhesives, and textiles; derivatives of these polymers and copolymers find an even greater variety of uses. See, for example, W. Daniels, Kirk-Othmer *Encyclopedia of Chemical Technology*, 3rd Ed. Vol. 23, pp. 817–847 (1978) and C. E. Sumner and Joseph R. Zoeller, *Vinyl Acetate in Acetic Acid and Its Derivatives*, V. H. Agreda and J. R. Zoeller, eds., Marcel Dekker, N.Y., Chapter 12, pp. 225–240 (1993).

Most of the vinyl acetate currently produced is manufactured by adding acetic acid to ethylene (reaction I) and, to a lesser extent, by adding acetic acid to acetylene (reaction II).

(I) $CH_2=CH_2 + AcOH + \frac{1}{2}O_2 \rightarrow AcOCH=CH_2 + H_2O$ (II) $CH\equiv CH + AcOH \rightarrow AcOCH=CH_2$ wherein Ac=acetyl.

Both processes, however, have their disadvantages. The disadvantages of the acetylene process include both the scarcity of acetylene and safety concerns associated with its use. The vapor-phase ethylene process requires purified oxygen and must be operated under the explosion limits for the ethylene-oxygen-acetic acid mixture. Thus, the vapor phase process leads to low conversions due to the quantity of oxygen that can safely be present at any time. This requirement adds significant expense because of the inherently large recycle loops. The liquid-phase ethylene process employs a very corrosive environment, requiring expensive construction materials. The high initial purchase price of a liquid phase plant renders the liquid phase process less attractive than the vapor phase process.

A third process produces vinyl acetate by reacting acetic anhydride with acetaldehyde to generate ethylidene diacetate (reaction III) and cracking the product to acetic acid and vinyl acetate (reaction IV).

(III) $AcH + Ac_2O \rightleftharpoons (AcO)_2CHCH_3$  $K_{140°\ C.} = 25$ (IV) $(AcO)_2CHCH_3 \rightleftharpoons AcOH + AcOCH=CH_2$  $K_{140°\ C.} = 0.01$ wherein Ac=acetyl.

Although it was practiced commercially until very recently, this process fell into disuse because of the expense of acetic anhydride and several operating deficiencies. The process has been described extensively in the literature. See, for example, Kirk-Othmer *Encyclopedia of Chemical Technology*, cited above, U.S. Pat. Nos. 2,425,389 and 2,859,241, British Patent 2,013,184 A and *Hydrocarbon Processing and Petroleum Refiner*, Vol. 44 (11), p. 287 (1965). The operating deficiencies in the acetic anhydride-acetaldehyde process result from the fact that the reactions involved are equilibria; consequently, the components of reactions (III) and (IV) are present simultaneously in substantial quantities in the distillation train.

As designed and operated, the acetic anhydride-acetaldehyde process uses 5 major operating units. A schematic process is shown in Kirk-Othmer *Encyclopedia of Chemical Technology*, 3rd Ed. Vol. 23 (1978) at page 824. Kirk-Othmer depicts the following process steps: (1) reacting acetaldehyde and acetic anhydride in the presence of an acid catalyst to generate an equilibrium mixture of acetaldehyde, acetic anhydride, vinyl acetate, ethylidene diacetate and acetic acid (Reactor); (2) separating ethylidene diacetate, acetic anhydride, and catalyst from acetaldehyde, vinyl acetate, and acetic acid (Reactor tower); (3) separating acetaldehyde from vinyl acetate and acetic acid (Light-ends tower); (4) separating acetic acid coproduct from vinyl acetate (Acid-stripper tower); and (5) rectifying vinyl acetate (Vinyl acetate finishing tower). The depicted process also provides a purge for solids removal. The fact that the desired material is not the least volatile component, but a "mid-boiler," further complicates the process. Until the equilibria in reactions (III) and (IV) are terminated by physically separating the products from the catalyst or by neutralizing the catalyst, distillation favors producing the least volatile component, acetaldehyde. In order to drive the equilibrium toward forming vinyl acetate and to suppress back reactions to acetaldehyde, it was necessary to run the Reactor (1) at acetic anhydride to acetaldehyde ratios of at least 2:1 to 4:1 as described in U.S. Pat. No. 2,859,241 and the Reactor (1) and Reactor tower (2) at anhydride to ethylidene diacetate ratios of preferably 5:1 to 15:1 as specified in U.S. Pat. No. 2,425,389.

Advances in acetic anhydride technology over the last two decades, such as through carbonylating methyl acetate with carbon monoxide to produce acetic anhydride, have improved the cost of acetic anhydride production. This advance, coupled with the desire in the industry to convert to processes using carbon monoxide and, optionally, hydrogen (syngas), has led to a number of processes generating ethylidene diacetate. See, for example, the processes described in the *Vinyl Acetate* reference cited above and J. Gauthier-Lafaye and R. Perron, *Methanol and Carbonylation*, English Translation, Imprimerie CD Editions, Saint-Herblain, France, pp. 201–224 (1987). The object in each of these processes is to generate vinyl acetate monomer through existing technology. None of these publications, however, describes an improvement in an existing process and, therefore, the basic problems in converting acetaldehyde and acetic anhydride to vinyl acetate via ethylidene diacetate still exist.

SUMMARY OF THE INVENTION

The present invention provides a process for producing a vinyl carboxylate ester from a carbonyl compound and a carboxylic acid anhydride. The process comprises feeding a carboxylic acid anhydride to the middle portion of a reactive distillation column (RDC) while feeding a carbonyl compound to the lower section of the RDC and removing a product comprising the vinyl carboxylate ester. A carboxylic acid coproduct corresponding to the anhydride reactant may be removed from the upper section of the RDC with the vinyl carboxylate ester, or from the upper section of the RDC as a separate side draw. Unreacted carbonyl may be removed from the RDC from the top along with the vinyl carboxylate ester or separately removed and recycled to the bottom portion of the RDC. Unreacted anhydride and an alkylidene dicarboxylate may be removed from the base of the RDC and recycled to the middle portion of the RDC. The product vinyl carboxylate may be further purified in one or two additional distillation vessels.

The Figures are described in further detail below.

DETAILED DESCRIPTION OF THE INVENTION

As noted above, the present invention is a novel process for generating vinyl esters of aliphatic carboxylic acids. In the present invention, a vinyl carboxylate ester is produced by reacting a carbonyl compound, such as an aldehyde or a ketone, and an anhydride of a carboxylic acid in a reaction zone in a reactive distillation column. The vinyl carboxylate ester is then recovered and substantially separated from other compounds in a distillation zone.

We have developed an improved process to produce vinyl carboxylate esters, such as vinyl acetate, from carbonyl compounds and carboxylic acid anhydrides wherein the unit operations are reduced (i.e., less equipment is required). Reducing the unit operations decreases significantly both the initial cost and the cost of operating a plant. These advantages are provided by using a countercurrent reactive distillation step for forming and separating initially the vinyl carboxylate product.

The process of the present invention produces a vinyl carboxylate ester which comprises feeding an aliphatic carboxylic acid anhydride of the formula where $R^1$ is an alkyl of 1 to 5 carbon atoms, to the middle section of an RDC; feeding an aliphatic carbonyl compound of the formula where $R^2$ is alkyl of 1 to 5 carbon atoms, $R^3$ is methyl or ethyl, and $R^4$ is alkyl of 1 to 4 carbon atoms, provided that the total carbon content of $R^3$ and $R^4$ is not more than 5, to the bottom section of the RDC; and removing a product stream comprising a vinyl carboxylate ester of the formula where $R^1$ is defined as above, $R^5$ and $R^6$ are each, independently, hydrogen or alkyl of up to 4 carbon atoms provided that the total carbon content of $R^5$ and $R^6$ does not exceed 4 carbon atoms, $R^7$ is hydrogen or alkyl of up to 3 carbon atoms, and $R^8$ is alkyl of 1 to 4 carbon atoms provided that the total carbon content of $R^7$ and $R^8$ does not exceed 4 carbon atoms, from the upper section of the RDC.

The vinyl carboxylate ester product may be purified in at least one additional distillation vessel.

In the process described, the anhydride and carbonyl flow counter-currently to each other in the presence of an acid catalyst within the lower half of the RDC, and the temperature at the base of the RDC is maintained at the boiling point of the anhydride plus from about 0° C. to about 50° C. and the temperature at the top of the RDC is maintained at a temperature of 55° C. below or 70° C. above the boiling point of the vinyl carboxylate ester.

The process further provides for removing coproduced carboxylic acid from the top of the RDC in the product stream along with the vinyl carboxylate ester. In the alternative, the carboxylic acid may be removed as a separate product from the upper section of the RDC at a point below the removal point of the vinyl carboxylate ester. Unreacted carbonyl may also be removed from the top of the RDC in the product stream, or may be removed from the top of the RDC as a separate product and recycled to the bottom section of the RDC; the unreacted carbonyl may be further purified prior to reintroducing it to the RDC.

The present process also provides for removing a stream comprising unreacted anhydride and an alkylidene dicarboxylate of the formula where $R^1$–$R^4$ are as defined above, from the base of the RDC and recycling the stream to the middle section of the RDC. As noted below, the acidic catalyst may be recycled to the middle section of the RDC along with the unreacted anhydride and alkylidene dicarboxylate.

Thus an embodiment of this invention is a process for producing a vinyl carboxylate ester comprising:

(1) feeding an aliphatic carboxylic acid anhydride to the middle section of a reactive distillation column (RDC);

(2) feeding an aliphatic carbonyl compound such as an aldehyde containing 2 to 6 carbon atoms or a ketone containing 3 to 6 carbon atoms to the bottom section of the RDC;

(3) removing a stream comprising the vinyl carboxylate ester from the upper section of the RDC;

(4) removing a carboxylic acid corresponding to the anhydride fed in step (1), from the upper section of the RDC as part of the product stream in step (3) or, optionally, as a separate product from the upper section of the RDC at a point below the removal point of the vinyl carboxylate ester product in step (3);

(5) removing unreacted carbonyl compound from the upper section of the RDC as part of the product stream in step (3) or, optionally, as a separate product from the top of the RDC and recycling, optionally after further purification, the removed unreacted carbonyl compound to the bottom section of the RDC;

(6) removing a stream comprising the anhydride of (1) and an alkylidene dicarboxylate derived from the anhydride and carbonyl compounds from the base of the RDC and recycling the stream to the middle section of the RDC; and (7) further purifying the vinyl carboxylate ester in step (3) in 1 or 2 additional distillation vessels to obtain a product comprising vinyl carboxylate ester;

wherein an acidic catalyst is maintained within the lower half of the RDC, the temperature at the base of the RDC is maintained at a temperature which is equal to the boiling point of the anhydride plus from 0° C. to 50° C., and the temperature at the top of the RDC is maintained at a temperature which is equal to the boiling point of the vinyl carboxylate ester minus 55° C. to plus 70° C.

In the present process, the anhydride and carbonyl compounds flow counter-currently and react in the presence of an acidic catalyst throughout a reaction zone of the RDC to form an alkylidene dicarboxylate according to reaction (III) above. The alkylidene dicarboxylate thus formed is the highest boiling component in the mixture and is rapidly driven toward the lower section (i.e., highest temperature) of the reaction zone, where it cracks according to reaction (IV), to form a vinyl carboxylate ester and an aliphatic carboxylic acid corresponding to the aliphatic, carboxylic acid anhydride fed in step (1) above. Reaction (IV) above, occurs to some extent throughout the reaction zone, but primarily in the lower half. The products of reaction (IV), the vinyl carboxylate ester and the aliphatic carboxylic acid, are lower boiling than either the anhydride or the alkylidene dicarboxylate and are thus driven from the reaction zone to the upper, distillation section of the RDC where they can be obtained as product.

Most of the ascending carbonyl compound is trapped or reacted with the descending anhydride; however, excess carbonyl compound may be removed from the upper section of the RDC with the vinyl carboxylate product stream or, optionally, as a separate top product from the RDC. As will be described in more detail below, the vinyl carboxylate product obtained from the RDC may be purified by distilling in 1 or 2 distillation vessels to remove carboxylic acid coproduct, any carbonyl compound, and possibly minor amounts of the anhydride to provide a vinyl carboxylate ester having a purity of 98% or greater.

The present invention proceeds through the same chemical reactions as described by Kirk-Othmer *Encyclopedia of Chemical Technology,* 3rd Ed. Vol. 23, p.824 (1978) and by *Hydrocarbon Processing and Petroleum Refiner,* Vol. 44 (11), p.287 (1965). However, the present invention, which uses a reactive distillation column, clearly entails significantly less equipment than the process depicted on page 824 of Vol. 23 of Kirk-Othmer *Encyclopedia of Chemical Technology,* 3rd Ed. (1978). In addition, the present invention requires significantly lower ratios of reactants in order to achieve the same level of conversion to vinyl carboxylate than the process described in U.S. Pat. Nos. 2,425,389 and 2,859,241. Further, the present invention produces substantially no saturated carboxylate ester impurity in the vinyl carboxylate ester product. By contrast, the conventional vapor phase ethylene process to make vinyl acetate produces ethyl acetate, a significant and difficult to remove impurity in the vinyl acetate product as described in Ullmann's *Encyclopedia of Industrial Chemistry,* 5th Ed. Vol. A27, p.824 (1996).

The aliphatic carboxylic acid anhydrides of the present process may contain from 4 to 12 carbon atoms. Typical carboxylic anhydrides have the formula wherein $R^1$ is alkyl of 1 to 5 carbon atoms. Propionic and, especially, acetic anhydride are preferred.

The aliphatic carbonyl reactant may be an aliphatic aldehyde containing 2 to 6 carbon atoms or an aliphatic ketone containing 3 to 6 carbon atoms. Examples of such aldehydes and ketones are encompassed by the formulas wherein $R^2$ is alkyl of 1 to 5 carbon atoms, $R^3$ is methyl or ethyl, and $R^4$ is alkyl of 1 to 4 carbon atoms, provided that the total carbon content of $R^3$ and $R^4$ is not more than 5.

The carboxylic acid anhydride and carbonyl compound react in the presence of an acidic catalyst to form an alkylidene dicarboxylate ester such as those having the formulas wherein $R^1$, $R^2$, $R^3$ and $R^4$ are as defined above. The alkylidene dicarboxylate ester is cracked, or decomposed, to form a vinyl carboxylate ester and an aliphatic carboxylic acid in the distillation zone within the RDC. These vinyl carboxylate esters and aliphatic carboxylic acids are illustrated by the formulas wherein $R^1$ is defined above, $R^5$ and $R^6$ are each, independently, hydrogen, or an alkyl of 1 to 4 carbon atoms provided that the total carbon content of $R^5$ and $R^6$ does not exceed 4, $R^7$ is hydrogen or alkyl up to 3 carbon atoms, and $R^8$ is alkyl of 1 to 4 carbon atoms provided that the total carbon content of $R^7$ and $R^8$ does not exceed 4 carbon atoms.

In the present invention, the carbonyl compound is fed to the bottom section of the reactive distillation column, e.g., in the reboiler or into the side of the column at a point no higher than one or two theoretical equilibrium stages below the aliphatic carboxylic acid anhydride feed. Preferably the carbonyl compound is fed to the reboiler or at a point 1 to 5 theoretical equilibrium stages above the reboiler. Most preferably the carbonyl compound is fed to the reboiler. If desired, the carbonyl compound may be fed to the column at a plurality of points.

The aliphatic carboxylic acid anhydride is fed to middle section of the RDC. The middle section of the RDC may be defined as the section of the column above the carbonyl feed and at least 1 to 2 theoretical equilibrium stages, preferably 5 to 40 theoretical equilibrium stages below the vinyl carboxylate product draw-off, more preferably 15 to 25 stages. If desired, the carboxylic acid anhydride may be fed to the column at a plurality of points.

It is important for proper column operation, and in order to lower the required ratio of reactants to achieve high conversion of reactants, that the anhydride feed is above the carbonyl feed and the two feeds are separated by at least 1 to 2 theoretical equilibrium stages, preferably 5 to 45 theoretical equilibrium stages, more preferably 15 to 30 stages.

The carboxylic anhydride and carbonyl compound are fed to the RDC at rates that maintain a carbonyl compound:anhydride molar ratio of about 0.25:1 to 6:1, preferably about 1:1 to 3:1, more preferably about 1:1 to 1.75:1.

As noted above, the anhydride and carbonyl will form some alkylidene dicarboxylate that falls to the bottom of the column without cracking.

A mixture comprising the carboxylic acid anhydride, alkylidene dicarboxylate and, if used, homogeneous catalyst is removed continuously from the bottom of the column (underflowed) and recycled to the middle section of the column to further react. This recycle stream may be fed in any of the locations specified for the fresh anhydride feed as described above. If necessary, some or all of the underflow may be subjected to a purification to remove sludge/high boilers formed in the process. Typically, a portion of the column underflow is passed through a heat exchanger (reboiler) and returned to the lower section of the column to provide heat to operate the process.

The acidic catalyst present in the reaction zone may be a homogeneous acid of low or negligible volatility such as a sulfonic acid. Examples include alkylsulfonic acids containing up to 10 carbon atoms or aromatic sulfonic acids such as benzenesulfonic acid and toluenesulfonic acid. Further, the acidic catalyst may be a solid, insoluble inorganic acid, such as alumina silicate or a titanium oxide. The acidic catalyst may also be selected from acidic heterogeneous materials such as acidic ion exchange resins. Examples of such resins include sulfo-bearing, styrene-divinylbenzene polymeric materials, Montmorillonite clays, silica-aluminas, titania, and the like. The homogeneous catalyst, when used, normally is removed from the base of the RDC with unreacted carboxylic anhydride and both recycled to the column.

During continuous operation of the process, the temperature at the base of the column is maintained at the boiling point of the carboxylic anhydride plus about 0° C. to 50° C. When using acetic anhydride and acetaldehyde reactants and operating at atmospheric pressure, the temperature at the base normally is about 140° C. to about 165° C., preferably about 145° C. to about 155° C. These base temperatures typically produce temperatures at the top of the column that are equal to the boiling point of the vinyl carboxylate ester minus about 55° C. to plus about 70° C. When using acetic anhydride and acetaldehyde reactants and operating at atmospheric pressure, the temperature at the top of the column normally is about 25° C. to 90° C., preferably about 40° C. to 80° C. The process of our invention may be carried out at pressures of about 0.25 to about 10 bars absolute, preferably with operating pressures being between about 1 and about 5 bars absolute, more preferably about 2.5 to about 4.5 bars absolute.

The reactive distillation column used in the present invention comprises a reaction zone and a distillation zone. Generally, the reaction zone is the volume within the column between the carbonyl compound feed up to the carboxylic anhydride feed. Although some reaction may occur above the reaction zone, the acidic catalyst is maintained within the reaction zone where most alkylidene dicarboxylate and vinyl carboxylate formation takes place. The column interior above the reaction zone is the distillation zone where the co-products vinyl carboxylate ester and carboxylic acid are separated from high boiling materials and removed from the column.

The vinyl carboxylate ester and carboxylic acid are removed as overhead products with any excess carbonyl compound or, optionally, can be withdrawn from the distillation zone as a sidedraw below the carbonyl compound overhead product. The vinyl carboxylate ester and carboxylic acid are withdrawn from the distillation zone, typically at a point at least 1 to 2 theoretical equilibrium stages, preferably 5 to 40 theoretical equilibrium stages above the anhydride feed point, more preferably 15 to 25 theoretical stages above the anhydride feed point and 0 to 20 theoretical equilibrium stages below where the excess carbonyl compound is withdrawn, preferably 0 to 15 stages below where the excess carbonyl compound is withdrawn.

Alternatively, because the carboxylic acid is an intermediate boiler between the vinyl carboxylate and anhydride, the carboxylic acid can be made to band at high concentration in the distillation zone. Thus, carboxylic acid may be removed as a separate sidedraw below the vinyl carboxylate product take-off point. The carboxylic acid sidedraw may be further purified in a side stripper column with the overheads returned to the main reactive distillation column in order to produce high purity carboxylic acid as a separate product. If the carboxylic acid is removed as a separate sidedraw lower in the distillation zone, the vinyl carboxylate may be made to band higher in the distillation zone and may similarly be removed as a sidedraw in high concentration and, optionally, separated from unreacted carbonyl compound in a side stripper.

The vinyl carboxylate product stream withdrawn from the RDC typically contains, in addition to vinyl carboxylate, from about 0 to 60 molar percent of coproduct carboxylic acid, 0 to 75 molar percent unreacted carbonyl compound and up to about 5 molar percent of other materials such as high boiling anhydride and alkylidene dicarboxylate. More typically the vinyl carboxylate product stream comprises vinyl carboxylate and carboxylic acid in about a 1:1 molar ratio and 15 to 30 mole percent unreacted carbonyl compound.

In order to achieve high conversion of the anhydride reactant, e.g., at least 75 mole percent, preferably greater that 90 mole percent, more preferably greater than 95 mole percent conversion, the reaction zone of the reactive distillation column is equipped with gas/liquid contacting devices known in the art to provide high interfacial area and high residence time. When using a homogeneous catalyst, e.g., benzenesulfonic acid, the reaction zone may be equipped with conventional reverse flow trays having high weirs, high bubble cap risers, and large inlet and flow reversing zone sumps as described in U.S. Pat. No. 4,535,595. When using a heterogeneous catalyst,e.g., acidic ion exchange resins, the reactive zone may be equipped with a perforated plate which allows for the passage of gases and liquids and provides support for and retention of randomly packed catalyst particles as described in U.S. Pat. No. 5,338,518 or catalytic bales or bags as described in detail in U.S. Pat. Nos. 4,215,011, 4,232,177, 4,242,530, and 4,443,559. Other embodiments of suitable reactive distillation gas-liquid contactors for both homogeneous and heterogeneous catalysts are possible.

The residence time of the reaction mixture in the column required for a satisfactory conversion rate can vary significantly depending on other process variables such as the particular catalyst and the amount or concentration being used, column pressure (and resulting temperature), and the ratio of carbonyl compound to anhydride. As used herein, "residence time" is the liquid hold-up volume in the reaction zone trays divided by the average liquid volumetric flowrate of the reaction mixture in the reaction zone. Normally, residence time will be at least 15 minutes, preferably in the range of 20 minutes to 60 minutes.

The distillation zone of the reactive distillation column is provided with any gas/liquid contacting device known in the art suitable for conventional distillation practice. The gas/liquid contacting equipment in the distillation zone may include, but is not limited to, cross-flow sieve, valve, or bubble cap trays, structured packings such as Mellapak®, Flexipac®, Gempak®, Goodloe®, Sulzer®, or random or dumped packing, such as berl saddles, Intalox® saddles, raschig rings, Pall® rings, and Nutter Rings®. These and other types of suitable gas/liquid contacting equipment are described in Kister, H. Z. *Distillation Design,* McGraw-Hill, New York (1992), Chapters 6 and 8.

During the process, it is desirable to add a polymerization inhibitor, such as to the RDC to prevent or inhibit polymer formation. The polymerization inhibitor may be added in any convenient manner. The polymerization inhibitor may be a phenolic or copper compound such as a hindered phenol or hydroquinone, a derivative of hydroquinone or copper salts. Alternatively, a copper packing material may be used in the distillation zone, eliminating any need for the addition of a polymerization inhibitor.

The vinyl carboxylate product stream withdrawn from the RDC may be further purified by fractional distillation in 1 or 2 distillation operations. For example, if the vinyl carboxylatecarboxylic acid product and excess carbonyl compound are removed as a single top product from the RDC, the product stream may be fed to the side, e.g., within the middle section, of a carbonyl compound separating column to remove excess carbonyl compound from the top of the column and to remove (i.e., under flow) vinyl carboxylate, carboxylic acid, and any minor heavy impurities such as carboxylic acid anhydride from the base or bottom of the column. Typically, the base temperature of the carbonyl compound separating column is maintained at a temperature equal to the boiling point of the vinyl carboxylate plus about 10° C. to 30° C. The temperature of the top of the column normally is equal to the boiling point of the carbonyl compound plus 0° C. to 35° C. The carbonyl compound may then be recycled in part or whole to the RDC, at any point that fresh carbonyl feed can be fed to the RDC.

The combined vinyl carboxylate and carboxylic acid underflow from the carbonyl compound separating column, which typically is about a 1:1 molar ratio of vinyl carboxylate to carboxylic acid, is then subjected to a further finishing distillation step to remove the vinyl carboxylate from the top of the column and to remove the carboxylic acid and any minor heavy impurities such as carboxylic acid anhydride from the base or bottom of the column. The vinyl carboxylate/carboxylic acid stream is fed to the side, typically within the middle section of the finishing column. The base temperature of the finishing column is maintained at a temperature equal to the boiling point of the carboxylic acid plus about 0° C. to 20° C. The temperature of the top of the finishing column normally is equal to the boiling point of the vinyl carboxylate ester plus or minus about 10° C., more normally plus or minus about 5° C. Both the carbonyl separation column and the finishing column may be operated at pressures similar to the pressures at which the reactive distillation column is operated. The vinyl carboxylate product having a purity of at least 98%, preferably at least 99%, more preferably at least 99.5%, is obtained from the finishing column either as a top product or, optionally, as sidedraw from a point on the column above the feed point of the feed materials and near the top of the vessel.

Figure 1:
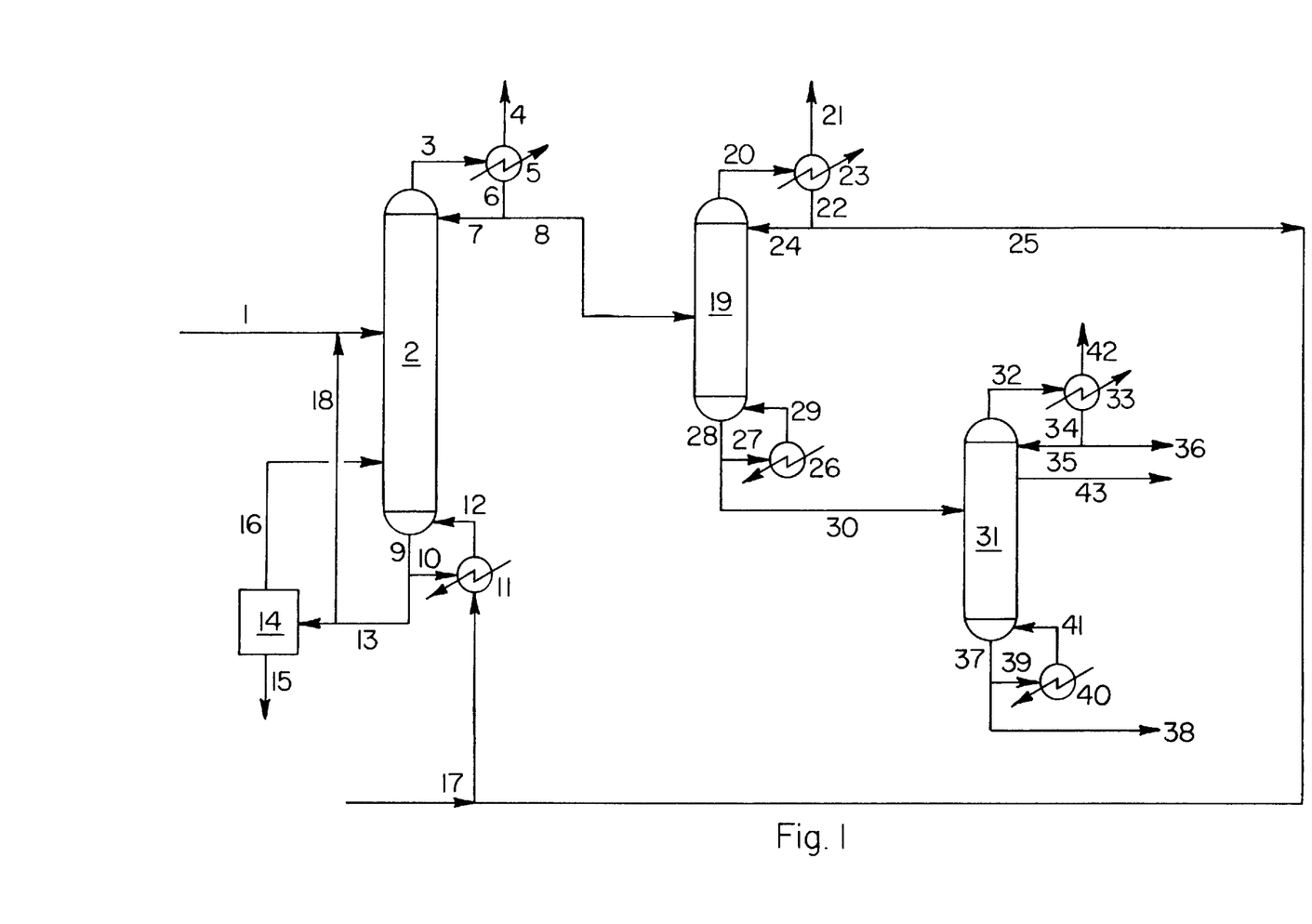
FIG. 1 illustrates an embodiment of the present invention and indicates appropriate apparatus for use therein.
Figure 2:
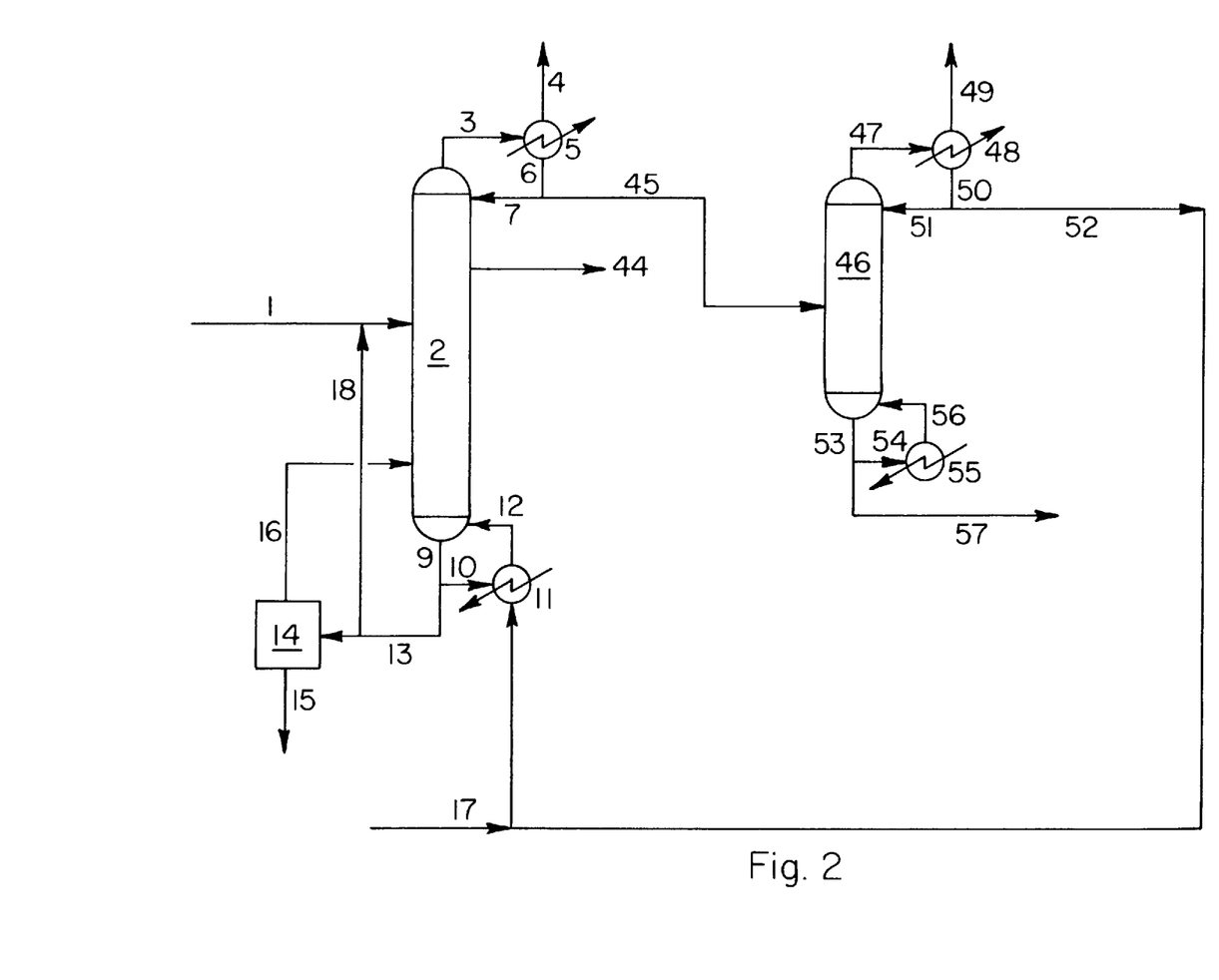
FIG. 2 illustrates the present invention wherein carboxylic acid coproduct from the RDC is drawn off as a separate side draw.
Figure 3:
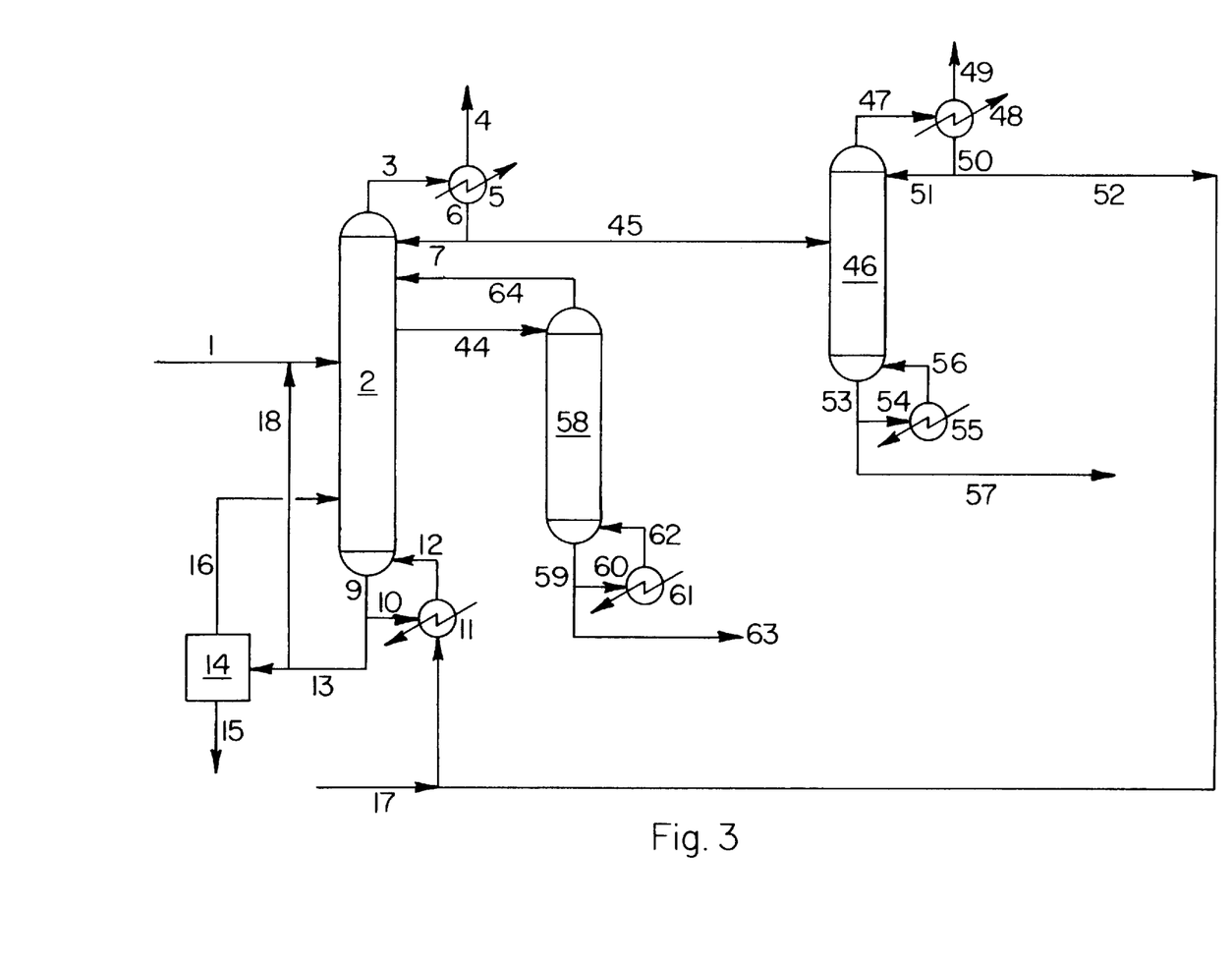
FIG. 3 illustrates the present invention wherein the carboxylic acid coproduct is drawn off and purified.

The accompanying FIGS. 1, 2, and 3 are process flow diagrams illustrating three systems embodying the principles of the present invention. It is, of course, possible that the vinyl carboxylate process may be operated by modifying the specific processes illustrated by the Figures. While the illustrated processes may be used to manufacture various vinyl carboxylate esters, the Figures are described herein for the production of vinyl acetate from acetaldehyde and acetic anhydride. The boiling points at 1 atmosphere of the materials involved in the process are:

| | |
|---|---|
| acetic anhydride = 140.0° C. | acetic acid = 118.0° C. |
| vinyl acetate = 73.3° C. | acetaldehyde = 20.4° C. |
| ethylidene diacetate = 164.4° C. | |

Referring to FIG. 1, acetic anhydride is fed through conduit 1 to the middle section of reactive distillation column (RDC) 2. When using a homogeneous catalyst,e.g., benzenesulfonic acid, fresh homogeneous catalyst is mixed with the acetic anhydride and co-fed through conduit 1. Fresh acetaldehyde in line 17 is mixed with recycled acetaldehyde in line 25 and fed to the lower section of the RDC through heat exchanger 11 and line 12. A liquid underflow stream comprising acetic anhydride, ethylidene diacetate, minor amounts of acetic acid, vinyl acetate, high boiling tars and sludge, and homogeneous catalyst, if present, is removed continuously from the RDC through line 9 and a portion, e.g., from 10 to 95 weight percent, is recycled to the RDC via line 10, heat exchanger 11, and line 12. The remainder of the liquid column underflow is fed by line 13 to sludge removal unit 14 wherein a minor amount of sludge and high boilers is removed, e.g., by evaporation in a wiped film or thin film evaporator from the system via line 15. The low boiling stream from the sludge removal unit 14 is recycled to the RDC through conduit 16. Alternatively, a portion, e.g., from about 50 to 95 weight percent, of the underflow stream 13 may be recycled directly to the middle section of RDC 2 by means of conduit 18. In this variation of the process, only a minor portion of the column 2 underflow normally is fed to sludge removal unit 14.

The portion of the RDC between the feed points of the acetic anhydride 1 and acetaldehyde 12 is the reaction section of the column where the ascending acetaldehyde contacts and reacts with the descending acetic anhydride to form ethylidene diacetate. The ethylidene diacetate is in equilibrium with vinyl acetate and acetic acid according to reaction IV set forth above. The reaction zone is equipped with gas/liquid contacting devices known in the art to provide high interfacial area and high residence time. When using a homogeneous catalyst the reaction zone may be equipped with conventional reverse flow trays having high weirs, high bubble cap risers, and large inlet and flow reversing zone sumps as exemplified and described in detail in U.S. Pat. No. 4,535,595. When using a heterogeneous catalyst, e.g., acidic ion exchange resins, the reactive zone may be equipped with a perforated plate which allows for the passage of gases and liquids and provides support for and retention of randomly packed catalyst particles as described in U.S. Pat. No. 5,338,518 or catalytic bales or bags as described in detail in U.S. Pat. Nos. 4,215,011, 4,232,177, 4,242,530, and 4,443,559. Other embodiments of suitable reactive distillation gas-liquid contactors for both homogeneous and heterogeneous catalysts are possible.

Vaporous vinyl acetate and acetic acid, along with unreacted acetaldehyde rise in the RDC, passing out of the reaction section and into the distillation section of the column, which is the portion of the column between the point of the acetic anhydride feed 1 and the top of the column. The distillation section is provided with any gas/liquid contacting device known in the art suitable for conventional distillation practice. The gas/liquid contacting equipment in the distillation zone may include, but is not limited to cross-flow sieve, valve, or bubble cap trays, structured packings such as Mellapak®, Flexipac®, Gempak®, Goodloe®, Sulzer®, or random or dumped packing, such as berl saddles, Intalox® saddles, raschig rings, Pall® rings, and Nutter Rings®. These and other types of suitable gas/liquid contacting equipment is described in detail in Kister, H. Z. *Distillation Design,*McGraw-Hill, New York (1992), Chapters 6 and 8.

A gaseous overhead stream comprising acetaldehyde, vinyl acetate, acetic acid, and minor amounts of acetic anhydride is removed continuously from RDC 2 through conduit 3 and fed to heat exchanger 5 to condense a portion of the stream and to remove uncondensable components from the system by means of conduit 4. A portion, e.g., from 50 to 95 weight percent, of the condensed material produced in heat exchanger 5 is recycled to the upper section of RDC 2 via lines 6 and 7 as reflux. The remainder of the condensed material is fed via conduit 8 to the side of an acetaldehyde recovery column 19. This column is operated at a base temperature of about the boiling point of vinyl acetate plus about 10° to 40° C. and a head temperature of about the boiling point of acetaldehyde plus 0° to 35° C. and is equipped with any gas/liquid contacting device known in the art suitable for conventional distillation practice. The gas/liquid contacting equipment may include, but is not limited to cross-flow sieve, valve, or bubble cap trays, structured packings such as Mellapak®, Flexipac®, Gempak®, Goodloe®, Suizer®, or random or dumped packing, such as berl saddles, Intalox® saddles, raschig rings, Pall® rings, and Nutter Rings®.

Most of the acetaldehyde fed to column 19 is removed from column 19 as a vapor from the top of the column through conduit 20 and condensed in heat exchanger 23. Uncondensed gases are purged from the system through line 21. The condensed material typically consists of 90+weight percent acetaldehyde with the remainder comprising vinyl acetate and acetic acid. A portion of this stream, e.g., from 55 to 75 weight percent, of the condensed material produced in heat exchanger 23 is recycled to the upper section of column 19 via lines 22 and 24 as reflux. The remainder of the condensed material is recycled to RDC 2 via line 25.

The underflow product in line 28 from column 19 comprises product vinyl acetate and co-product acetic acid and is split with a portion sent via line 27 to heat exchanger 26 and returned to the lower section of column 19 via line 29 as boil-up. The remainder of the underflow product 28 is fed through conduit 30 to the side of a vinyl acetate finishing column 31. The base of finishing column 31 is maintained at a temperature equal to the boiling point of acetic acid plus about 0° C. to 20° C. The temperature at the top of the finishing column normally is equal to the boiling point of the vinyl acetate plus or minus about 10° C., more normally plus or minus about 5° C. Column 31 is equipped with any gas/liquid contacting device known in the art suitable for conventional distillation practice. The gas/liquid contacting equipment may include, but is not limited to, cross-flow sieve, valve, or bubble cap trays, structured packings such as Mellapak®, Flexipac®, Gempak®, Goodloe®, Sulzer®, or random or dumped packing, such as berl saddles, Intalox® saddles, raschig rings, Pall® rings, and Nutter Rings®.

The underflow product in line 37, from column 31, which comprises acetic acid and heavies, is split with a portion sent via line 39 to heat exchanger 40 and returned to the lower section of column 31 through line 41 as boil-up. The remainder of the underflow product 38 is removed as acetic acid co-product. Most of the vinyl acetate fed to column 31 is removed as a vapor from the top of the column through conduit 32 and condensed in heat exchanger 33. Uncondensed gases are purged from the system through line 42. The condensed material typically consists of 99+weight percent vinyl acetate. A portion of this stream, e.g., from 30 to 95 weight percent, of the condensed material produced in heat exchanger 32 is recycled as reflux to the upper section of column 31 via lines 34 and 35. The vinyl acetate product having a purity of at least 98%, preferably at least 99%, more preferably at least 99.5%, is obtained from the finishing distillation column 31 either as stream 36, or optionally as sidedraw 43 from a point on column 31 above the feed point of line 30 and near the top of the vessel. Both column 31 and column 19 may be operated at pressures similar to the pressure in RDC 2.

In the process flow diagram depicted in FIG. 2, the reactive distillation section of reactive distillation column 2, associated feed and underflow conduits (lines 1, 9, 10, 12, and 17) and heat exchanger 11, and conduits and equipment associated with sludge removal unit 14 are operated in substantially the same manner as described above with respect to FIG. 1. The process in FIG. 2 provides for removal of acetic acid co-product from the distillation section of RDC 2 as a separate sidedraw stream in line 44.

The acetic acid is an intermediate boiler between the vinyl acetate and acetic anhydride; the acetic acid can be made to band at high concentration in the upper section of the distillation zone of RDC 2. The carboxylic acid may be largely removed as a separate sidedraw 5 to 20 theoretical stages, preferably 10 to 15 stages below the top of RDC 2. The acetic acid sidedraw in line 44 is typically comprised of 90 to 97 weight percent acetic acid and 0.5 to 5.0 weight percent each of vinyl acetate and acetic anhydride.

Vinyl acetate and acetaldehyde, essentially free of acetic acid, is continuously withdraw from RDC 2 as a vapor via line 3 and fed to heat exchanger 5 to condense a portion of the stream and to remove uncondensible components from the system by conduit 4. A portion, e.g., from 50 to 95 weight percent, of the condensed material produced in heat exchanger 5 is recycled to the upper section of RDC 2 via lines 6 and 7 as reflux. The remainder of the condensed material is fed via conduit 45 to the side of vinyl acetate refining column 46. This column is operated at a base temperature of about the boiling point of vinyl acetate plus about 0° to 15° C. and a head temperature of about the boiling point of acetaldehyde plus 0° to 25° C. and is equipped with any gas/liquid contacting device known in the art suitable for conventional distillation practice. The gas/liquid contacting equipment may include, but is not limited to, cross-flow sieve, valve, or bubble cap trays, structured packings such as Mellapak®, Flexipac®, Gempak®, Goodloe®, Sulzer®, or random or dumped packing, such as berl saddles, Intalox® saddles, raschig rings, Pall® rings, and Nutter Rings®.

Most of the acetaldehyde fed to column 46 is removed as a vapor from the top of the column through conduit 47 and condensed in heat exchanger 48. Uncondensed gases are purged from the system through line 49. The condensed material typically consists of 90+ weight percent acetaldehyde with the remainder comprising vinyl acetate. A portion of this stream, e.g., from 55 to 75 weight percent, of the condensed material produced in heat exchanger 48 is recycled to the upper section of column 46 as reflux via lines 50 and 51. The remainder of the condensed material is recycled to RDC 2 via line 52.

The underflow product, line 53, from column 46 comprising product vinyl acetate is split with a portion sent via line 54 to heat exchanger 55 and returned to the lower section of column 46 via line 56 as boil-up. The remainder of the underflow product 53 is withdrawn through conduit 57 as highly purified vinyl acetate comprising at least 98%, preferably at least 99%, more preferably at least 99.5 weight percent vinyl acetate.

In the process flow diagram depicted in FIG. 3, the reactive distillation column 2, vinyl acetate refining column 46, and associated conduits and equipment are operated in substantially the same manner as described above with respect to FIG. 2. The process in FIG. 2 provides for purification of the acetic acid co-product in sidedraw stream in line 44. Line 44 is fed to the side of reboiled stripping column 58. Column 58 is maintained with a bottom temperature of the boiling point of acetic acid plus 0° to 15° C. The vaporous overheads from column 58, comprising vinyl acetate and acetaldehyde are returned to RDC 2 via line 64 at a point above the withdrawal point of stream 44, typically in the vapor space of the same stage as the withdrawal point of stream 44.

The underflow product in line 59 from column 58, comprising co-product acetic acid, is split with a portion sent via line 60 to heat exchanger 61 and returned to the lower section of column 58 via line 62 as boil-up. The remainder of the underflow product 59 is withdrawn through conduit 63 as purified acetic acid comprising at least at least 95 weight percent acetic acid.

The process provided by the present invention is further illustrated by the following examples. The reactive distillation system used comprised a single column containing a reaction zone and a distillation zone. The reaction zone utilized 31 Oldershaw® trays, each being 19 mm (0.75 inch) in diameter by 32 mm (1.25 inches) high and having a 13 mm (0.5 inch) weir height. The distillation zone, which was mounted atop the reaction zone, consisted of 11 inches of stainless steel Goodloe® packing and one inch of copper Goodloe® packing in a 25 mm (1 inch) diameter column. A solenoid-actuated, liquid dividing takeoff head equipped with condenser and jacketed receiver was used to control reflux ratios and remove distillate. A circulating cooling bath was used to maintain the condenser and distillate receiver at 0°–50° C. One feed port was positioned at the top Oldershaw® tray and another feed port was positioned in the base. Sample ports were located in the base, at the 15th plate of the Oldershaw® column, and in the distillate receiver. Samples were analyzed by gas/liquid chromatography. The glass column, receiver, takeoff head, and base pot were designed to operate at pressures up to two atmospheres absolute. This apparatus and Examples 1–4 do not conform entirely to the process as described hereinabove. However, Examples 1–4 demonstrate the basic operation of a reactive distillation column to produce a vinyl carboxylate product. Furthermore, the operating data produced by Examples 1–3 were used in the computer-simulated operation of the process described in Examples5–10.

EXAMPLE 1

Acetic anhydride (250 g) containing 0.1 weight percent benzene sulfonic acid was charged initially to the base of the apparatus described above. The acetaldehyde feed was started and gradually increased to 12 ml per hour and allowed to reach steady state over 14.2 hours. Upon reaching steady state, feed rates were fixed at 9 mL per hour for acetic anhydride containing 1 weight percent benzenesulfonic acid and 12 mL per hour for acetaldehyde for the remainder of the experiment. This provides an acetaldehyde:acetic anhydride mole ratio of 2.3:1. An additional 18.4 hours of operation at these conditions produced an average of 8.9 g per hour vinyl acetate, 3.7 g per hour acetaldehyde, and 1.18 g per hour acetic acid in the overhead takeoff, which was operated to remove the distillation fraction boiling below or at 65° C.

EXAMPLE 2

The material contained in the base in Example 1 was used in this experiment. Acetic anhydride containing 1 weight percent benzenesulfonic acid was fed at 20.76 mL per hour while maintaining the acetaldehyde feed at 12 mL per hour. These feed rates gave an acetaldehyde:acetic anhydride feed ratio of 1:1. After operating 5.1 hours to adjust conditions, an additional 26.7 hours of operation produced an average of 11.5 g per hour vinyl acetate, 1.75 g per hour acetaldehyde, and 5.72 g per hour acetic acid in the overhead takeoff, which was operated to remove the distillation fraction boiling below or at 89° C.

EXAMPLE 3

To the base of the above-described apparatus were charged 160 g of acetic anhydride containing 1 weight percent benzenesulfonic acid, 55 g of ethylidene diacetate, and 35 g of acetic acid. The pressure within the reactive distillation column was maintained at approximately 2 bars absolute while feeding acetic anhydride at a rate of 41.4 mL per hour and acetaldehyde at a rate of 24.0 mL per hour. Operation over a period of 25.7 hours produced in the overhead takeoff, which was operated to remove the distillation fraction boiling below or at 110° C. an average of 23.1 g per hour vinyl acetate, 4.2 g per hour acetaldehyde, and 23.2 g per hour acetic acid.

EXAMPLE 4

To the base of the above described apparatus were charged 220 g of propionic anhydride and 40 g of propionic acid. The acetaldehyde feed was started and gradually increased to 8.36 ml per hour and allowed to reach steady state over 23.3 hours. Upon reaching steady state, feed rates were fixed at 19.28 mL per hour propionic anhydride containing 1 weight percent benzene sulfonic acid and 8.36 mL per hour acetaldehyde. An additional 22.7 hours of operations at these feed rates produced in the overhead takeoff, operated to remove the distillation fraction boiling below or at 80° C., an average of 2.4 g per hour vinyl propionate, 3.2 g per hour acetaldehyde, and 1.6 g per hour propionic acid.

In the following Examples 5–10, the process simulations were performed on Aspen® process simulating software version 9.2 by Aspen tech.

EXAMPLE 5

A series of computer simulations of the reactive distillation column described herein for the production of vinyl acetate from acetaldehyde and acetic anhydride were performed to determine the effect of the number of reaction stages on the required acetaldehyde to acetic anhydride feed ratio. Molar conversion of acetic anhydride was maintained at 99.9 percent, with a molar reflux ratio of 8, and a bottoms pressure of 3.5 atmospheres. Results are given in Table 1.

EXAMPLE 6

A series of computer simulations of the reactive distillation column described herein for the production of vinyl acetate from acetaldehyde and acetic anhydride were performed to determine the effect of the bottoms pressure on the required acetaldehyde to acetic anhydride feed ratio. Molar conversion of acetic anhydride was maintained at 99.9 percent, with a molar reflux ratio of 8. In all cases the number of theoretical stages was maintained at 35, with 11 reaction stages. Results are given in Table 2.

EXAMPLE 7

A series of computer simulations of the reactive distillation column described herein for the production of vinyl acetate from acetaldehyde and acetic anhydride were performed to determine the effect of acetaldehyde to acetic anhydride feed ratio on acetic anhydride conversion. A molar reflux ratio of 8 and a bottoms pressure of 4.14 atmospheres was chosen for all cases. The number of theoretical stages was maintained at 35, with 11 reaction stages. Results are given in Table 3.

EXAMPLE 8

A computer simulation of the embodiment of the vinyl acetate process shown in FIG. 1 was performed to obtain a material balance at a nominal production rate of 60,200 lb vinyl acetate per hour. Stream numbers correspond to those of FIG. 1. Results are given in Table 4.

EXAMPLE 9

A computer simulation of the embodiment of the vinyl acetate process shown in FIG. 2 was performed to obtain a material balance at a nominal production rate of 60,200 lb vinyl acetate per hour. Stream numbers correspond to those of FIG. 2. Results are given in Table 5.

EXAMPLE 10

A computer simulation of the embodiment of the vinyl acetate process shown in FIG. 1 was performed to obtain a material balance at a nominal production rate of 60,200 lb vinyl acetate per hour. Stream numbers correspond to those of FIG. 3. Results are given in Table 6.

TABLE 1

| Number of Reaction Stages | HAc/Ac2O Molar Ratio | Theoretical Stages | HAc Feed Stage | Ac2O Feed Stage | Ac2O Conversion | Ttop (°C.) | Tbot (°C.) |
|---|---|---|---|---|---|---|---|
| 3 | 16.186 | 28 | 28 | 25 | 0.999 | 56 | 194 |
| 5 | 2.585 | 30 | 30 | 25 | 0.999 | 76 | 190 |
| 8 | 1.587 | 33 | 33 | 25 | 0.999 | 92 | 190 |
| 11 | 1.427 | 35 | 35 | 25 | 0.999 | 97 | 190 |
| 19 | 1.288 | 43 | 43 | 25 | 0.999 | 103 | 190 |
| 26 | 1.278 | 50 | 50 | 25 | 0.999 | 103 | 190 |
| 46 | 1.276 | 70 | 70 | 25 | 0.999 | 104 | 194 |
| 76 | 1.274 | 100 | 100 | 25 | 0.999 | 104 | 194 |

TABLE 2

| Bottoms Pressure (Atm) | HAc/Ac2O Molar Ratio | Theoretical Stages | HAc Feed Stage | Ac2O Feed Stage | Ac2O Conversion | Ttop (°C.) | Tbot (°C.) |
|---|---|---|---|---|---|---|---|
| 1.5 | 2.442 | 35 | 35 | 25 | 0.999 | 40 | 154 |
| 2.5 | 1.692 | 35 | 35 | 25 | 0.999 | 75 | 179 |
| 3.5 | 1.427 | 35 | 35 | 25 | 0.999 | 97 | 190 |
| 4.14 | 1.407 | 35 | 35 | 25 | 0.999 | 105 | 197 |
| 4.5 | 1.424 | 35 | 35 | 25 | 0.999 | 108 | 200 |
| 6.5 | 1.973 | 35 | 35 | 25 | 0.999 | 111 | 216 |

TABLE 3

| Ac2O conv | HAc/Ac2O Molar Ratio | Theoretical Stages | HAc Feed Stage | Ac2O Feed Stage | Bottoms Pressure (Atm) |
|---|---|---|---|---|---|
| 1.000 | 1.726 | 35 | 35 | 25 | 4.14 |
| 0.999 | 1.407 | 35 | 35 | 25 | 4.14 |
| 0.950 | 1.345 | 35 | 35 | 25 | 4.14 |
| 0.900 | 1.287 | 35 | 35 | 25 | 4.14 |
| 0.800 | 1.177 | 35 | 35 | 25 | 4.14 |
| 0.600 | 0.983 | 35 | 35 | 25 | 4.14 |

|  | Flow Rates (lb/hr) | | | | |
| --- | --- | --- | --- | --- | --- |
| Stream Number | Acetaldehyde | Acetic Anhydride | Ethylidene Diacetate | Acetic Acid | Vinyl Acetate |
| 1 | — | 71463 | — | — | — |
| 8 | 10471 | 1205 | 0.0 | 41329 | 59840 |
| 13 | 5.53 | 1636 | 1800 | 79 | 19 |
| 17 | 30282 | — | — | — | — |
| 25 | 10466 | 0.001 | 0.0 | 0.03 | 598 |
| 30 | 5.2 | 1205 | 0.0 | 41329 | 59242 |
| 36 | 5.2 | 0.003 | 0.0 | 2.1 | 59183 |
| 38 | 0.0 | 1205 | 0.0 | 41327 | 59 |

TABLE 5

|  | Flow Rates (lb/hr) | | | | |
| --- | --- | --- | --- | --- | --- |
| Stream Number | Acetaldehyde | Acetic Anhydride | Ethylidene Diacetate | Acetic Acid | Vinyl Acetate |
| 1 | — | 71463 | — | — | — |
| 45 | 20489 | 0.02 | 0.0 | 80.9 | 58880 |
| 13 | 12.7 | 1086 | 2437 | 119 | 35.5 |
| 17 | 30754 | — | — | — | — |
| 52 | 20479 | 0.0 | 0.0 | 0.0 | 588 |
| 57 | 10.2 | 0.02 | 0.0 | 80.9 | 58291 |
| 44 | 168 | 1079 | 0.0 | 41344 | 1130 |

TABLE 6

|  | Flow Rates (lb/hr) | | | | |
| --- | --- | --- | --- | --- | --- |
| Stream Number | Acetaldehyde | Acetic Anhydride | Ethylidene Diacetate | Acetic Acid | Vinyl Acetate |
| 1 | — | 71463 | — | — | — |
| 45 | 20195 | 0.02 | 0.0 | 76 | 60217 |
| 13 | 13.5 | 1078 | 2452 | 117 | 35 |
| 17 | 30754 | — | — | — | — |
| 52 | 20185 | 0.0 | 0.0 | 0.0 | 602 |
| 57 | 10.2 | 0.02 | 0.0 | 76 | 59615 |
| 44 | 163 | 1021 | 0.0 | 41385 | 1130 |
| 64 | 163 | 0.0 | 0.0 | 2.1 | 1129 |
| 63 | 0.0 | 1021 | 0.0 | 41383 | 1.1 |

The invention has been described in detail with particular reference to preferred embodiments thereof, but it will be understood that variations and modifications can be effected within the spirit and scope of the invention.

We claim:

1. A process for producing a vinyl carboxylate ester comprising:

(1) feeding an aliphatic carboxylic acid anhydride of the formula to the middle section of a reactive distillation column (RDC);

(2) feeding an aliphatic carbonyl compound of the formula to the bottom section of the RDC; and (3) removing a product stream comprising a vinyl carboxylate ester of the formula from the upper section of the RDC;

wherein the anhydride and carbonyl flow countercurrently to each other in the presence of an acid catalyst within the lower half of the RDC and the temperature at the base of the RDC is maintained at the boiling point of the anhydride plus from about 0° C. to about 50° C. and the temperature at the top of the RDC is maintained at a temperature of 55° C. below or 70° C. above the boiling point of the vinyl carboxylate ester; and wherein $R^1$ is an alkyl of 1 to 5 carbon atoms, $R^2$ is alkyl of 1 to 5 carbon atoms, $R^3$ is methyl or ethyl, $R^4$ is alkyl of 1 to 4 carbon atoms provided that the total carbon content of $R^3$ and $R^4$ is not more than 5, $R^5$ and $R^6$ are each, independently, hydrogen, or an alkyl of 1 to 4 carbon atoms provided that the total carbon content of $R^5$ and $R^6$ does not exceed 4, $R^7$ is hydrogen or alkyl of up to 3 carbon atoms, and $R^8$ is alkyl of 1 to 4 carbon atoms provided that the total carbon content of $R^7$ and $R^8$ does not exceed 4 carbon atoms.

2. A process as claimed in claim 1 comprising the further step of removing a coproduced carboxylic acid that corresponds to the anhydride fed in Step 1 from the top of the RDC in the product stream, or removing said carboxylic acid from the RDC as a separate product from the upper section of the RDC at a point below the removal point of the vinyl carboxylate ester of Step 3.

3. A process as claimed in claim 2 which further comprises removing an unreacted carbonyl from the top of the RDC in the product stream, or removing unreacted carbonyl from the top of the RDC as a separate product and recycling, after optional further purification, the unreacted carbonyl to the bottom section of the RDC.

4. A process as claimed in claim 3 which further comprises removing a stream comprising unreacted anhydride and an alkylidene dicarboxylate of the formula wherein $R^1$–$R^4$ are as defined in claim 1, from the base of the RDC and recycling the unreacted anhydride and ethylidene dicarboxylate to the middle section of the RDC.

5. A process as claimed in claim 1 wherein the vinyl carboxylate ester is purified in at least one additional distillation vessel.

6. A process as claimed in claim 1 wherein the carboxylic acid anhydride is propionic anhydride or acetic anhydride.

7. A process as claimed in claim 6 wherein the carbonyl compound is acetaldehyde.

8. A process as claimed in claim 1 wherein the acid catalyst is a sulfonic acid or an acidic ion exchange resin.

9. A process as claimed in claim 8 wherein the acid is an alkylsulfonic acid having up to 10 carbon atoms or an aromatic sulfonic acid.

10. A process as claimed in claim 9 wherein the acid is benzenesulfonic acid or toluene sulfonic acid.

11. A process as claimed in claim 1 wherein the acid catalyst is a solid, insoluble inorganic acid.

12. A process as claimed in claim 1 wherein the molar ratio of carbonyl to anhydride is maintained at about 0.25:1 to 6:1.

13. A process as claimed in claim 12 wherein the ratio is maintained at about 1:1 to 3:1.

14. A process as claimed in claim 13 wherein the ratio is maintained at about 1:1 to 1.75:1.

15. A process as claimed in claim 1 wherein a polymerization inhibitor is added to the RDC.

16. A process for producing a vinyl carboxylate ester comprising:

(1) feeding an aliphatic carboxylic acid anhydride of the formula wherein $R^1$ is an alkyl of 1 to 5 carbon atoms to the middle section of a reactive distillation column (RDC);

(2) feeding an aliphatic carbonyl compound of the formula wherein $R^2$ is alkyl of 1 to 5 carbon atoms, $R^3$ is methyl or ethyl, and $R^4$ is alkyl of 1 to 4 carbon atoms, provided that the total carbon content of $R^3$ and $R^4$ is not more than 5, to the bottom section of the RDC; and (3) removing a stream comprising a vinyl carboxylate ester from the upper section of the RDC;

(4) removing a coproduced aliphatic carboxylic acid corresponding to the anhydride of step (1) from the upper section of the RDC as part of the product stream in step (3) or, optionally, removing the carboxylic acid as a separate product from the upper section of the RDC at a point below the removal point of the vinyl carboxylate ester in step (3);

(5) removing an unreacted carbonyl compound from the upper section of the RDC as part of the product stream in step (3) or, optionally, removing unreacted carbonyl as a separate product from the top of the RDC and recycling, after optional further purification, the unreacted carbonyl compound to the bottom section of the RDC;

(6) removing a stream comprising unreacted anhydride of step (1) and an alkylidene dicarboxylate derived from the anhydride of step (1) and the carbonyl compound of step (2) from the base of the RDC and recycling the stream to the middle section of the RDC; and (7) further purifying the vinyl carboxylate ester removed in step (3) in 1 or 2 additional distillation vessels to obtain a product comprising vinyl carboxylate ester;

wherein the anhydride and carbonyl flow countercurrently to each other in the presence of a sulfonic acidic catalyst selected from the group consisting of an alkylsulfonic acid of up to 10 carbon atoms and an aromatic sulfonic acid, within the lower half of the RDC, and the temperature at the base of the RDC is maintained at a temperature which is equal to the boiling point of the anhydride plus from about 0° C. to 50° C., and the temperature at the top of the RDC is maintained at a temperature of 55° C. below or 70° C. above the boiling point of the vinyl carboxylate ester.

17. A process as claimed in claim 16 wherein the molar ratio of carbonyl to anhydride is maintained at about 1:1 to 3:1.

18. A process as claimed in claim 17 wherein the anhydride is acetic anhydride, the carbonyl is acetaldehyde, the coproduced acid is acetic acid and the ester is vinyl acetate.

19. A process as claimed in claim 16 wherein the vinyl carboxylate ester has a purity of at least about 98%.

* * * * *